(12) United States Patent
Brahm

(10) Patent No.: US 10,583,219 B1
(45) Date of Patent: Mar. 10, 2020

(54) MULTILAYER BIOABSORBABLE CONSTRUCT AND METHODS OF USE

(71) Applicant: Brahm Holdings, LLC, Cordova, TN (US)

(72) Inventor: Timothy R. Brahm, Germantown, TN (US)

(73) Assignee: Brahm Holdings, LLC, Germantown, TN (US)

( * ) Notice: Subject to any disclaimer, the term of this patent is extended or adjusted under 35 U.S.C. 154(b) by 0 days.

(21) Appl. No.: 15/391,944

(22) Filed: Dec. 28, 2016

Related U.S. Application Data

(60) Provisional application No. 62/272,258, filed on Dec. 29, 2015.

(51) Int. Cl.
| | |
|---|---|
| *A61L 27/56* | (2006.01) |
| *A61L 27/58* | (2006.01) |
| *A61F 2/00* | (2006.01) |
| *A61L 27/36* | (2006.01) |
| *A61L 27/20* | (2006.01) |
| *A61L 27/38* | (2006.01) |

(52) U.S. Cl.
CPC ........ *A61L 27/3604* (2013.01); *A61F 2/0045* (2013.01); *A61F 2/0063* (2013.01); *A61L 27/20* (2013.01); *A61L 27/56* (2013.01); *A61L 27/58* (2013.01); *A61F 2210/0004* (2013.01); *A61F 2210/0076* (2013.01)

(58) Field of Classification Search
None
See application file for complete search history.

(56) References Cited

U.S. PATENT DOCUMENTS

| | | | | |
|---|---|---|---|---|
| 5,607,590 | A | * | 3/1997 | Shimizu ............... A61L 15/325 210/490 |
| 6,599,323 | B2 | * | 7/2003 | Melican ............... A61F 2/0045 424/426 |
| 8,323,701 | B2 | * | 12/2012 | Daniel ............... A61L 27/3604 424/583 |
| 8,961,617 | B2 | * | 2/2015 | Young ............... A61L 27/3604 623/23.72 |
| 9,770,472 | B1 | * | 9/2017 | Brahm ................... A61K 35/50 |
| 2007/0038298 | A1 | * | 2/2007 | Sulner ...................... A61F 2/18 623/10 |
| 2010/0082113 | A1 | * | 4/2010 | Gingras ............... A61L 31/005 623/23.72 |
| 2013/0253663 | A1 | * | 9/2013 | Amoroso ............... A61L 27/18 623/23.75 |
| 2014/0067058 | A1 | * | 3/2014 | Koob ..................... A61L 27/14 623/4.1 |

FOREIGN PATENT DOCUMENTS

WO   WO 07/010305   *   1/2007

OTHER PUBLICATIONS

Robson et al., Amniotic Membranes as Temporary Wound Dressings, Surgery, Gynecology, & Obstestrics, 1973, vol. 136 pp. 904-906. (Year: 1973).*

* cited by examiner

*Primary Examiner* — Allison M Fox
(74) *Attorney, Agent, or Firm* — Barnes & Thornburg LLP

(57) ABSTRACT

A multilayer bioabsorbable construct is provided that includes at least one top layer, at least one chorion membrane layer, at least one basement layer, and at least one support layer between the chorion membrane layer and basement layer. Various therapeutic uses of the multilayer bioabsorbable construct are also provided.

4 Claims, 1 Drawing Sheet

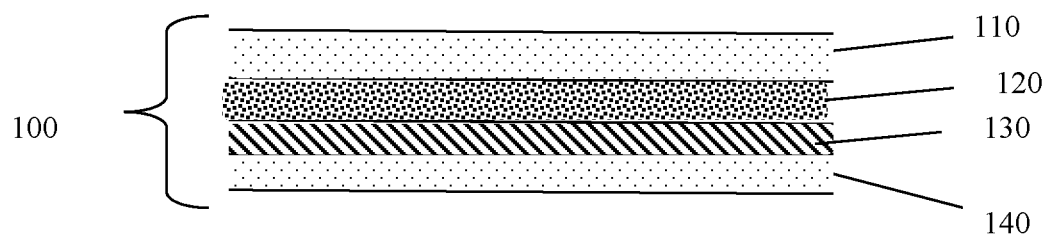

MULTILAYER BIOABSORBABLE CONSTRUCT AND METHODS OF USE

CROSS-REFERENCE TO RELATED APPLICATIONS

The present application claims prior to the U.S. provisional application No. 62/272,258 filed Dec. 29, 2016.

FIELD OF THE INVENTION

The present invention is directed to a multilayer bioabsorbable construct composed, in part, of aseptically recovered human birth tissue, as well as therapeutic methods of using the same.

BACKGROUND OF THE INVENTION

Human placental tissue has been used in various surgical procedures, including skin transplantation and ocular surface disorders, for over a century. The tissue has been shown to provide good wound protection, prevent surgical adhesions, reduce pain, reduce wound dehydration, and provide anti-inflammatory and anti-microbial effects.

The placenta is a fetomaternal organ consisting of a placental globe, umbilical cord, associated membranes (chorion membrane layer and amnion membrane layer), other gelatins, fluids, cells and extracellular material. The chorion membrane layer and the amnion membrane layer are attached by loose connective tissue and make up the placental sac. The innermost membrane of the placental sac is the amnion membrane layer, which comes into contact with the amniotic fluid that surrounds the fetus. The amnion membrane layer is avascular and lined by simple columnar epithelium overlying a basal membrane. The chorion membrane layer is the outermost layer of the sac and is heavily cellularized. The placental membranes have an abundant source of collagen that provides an extracellular matrix to act as a natural scaffold for cellular attachment in the body. Collagen provides a structural tissue matrix that facilitates, among other things, cell migration and proliferation in vivo.

SUMMARY OF THE INVENTION

According to one aspect, a multilayer bioabsorbable construct is provided. The construct includes at least one basement layer that includes:
  at least one basement layer comprising:
  (i) at least one amnion membrane layer, at least one chorion membrane layer, or at least one of both an amnion and chorion membrane layer that is/are processed in a manner that includes treatment with at least one alcohol composition; or
  (ii) at least one cross-linked amnion membrane layer, at least one cross-linked chorion membrane layer, or at least one of both a cross-linked amnion and cross-linked chorion membrane layer that is/are processed in a manner that includes treatment with a cross-linking solution; or
  (iii) at least one amnion membrane layer that is processed in a manner that includes treatment with at least one alcohol composition coupled with a fresh chorion membrane layer; or
  (iv) at least one cross-linked amnion membrane layer coupled with a fresh chorion membrane layer;
  at last one top layer comprising:
  (i) at least one amnion membrane layer, at least one chorion membrane layer, or at least one of both an amnion and chorion membrane layer that is/are processed in a manner that includes treatment with at least one alcohol composition; or
  (ii) at least one cross-linked amnion membrane layer, at least one cross-linked chorion membrane layer, or at least one of both a cross-linked amnion and cross-linked chorion membrane layer that is/are processed in a manner that includes treatment with a cross-linking solution; or
  (iii) at least one amnion membrane layer that is processed in a manner that includes treatment with at least one alcohol composition coupled with a fresh chorion membrane layer; or
  (iv) at least one cross-linked amnion membrane layer coupled with a fresh chorion membrane layer; and at least one support layer located between the basement and top layers.

According to one embodiment, the support layer includes bioabsorbable gauze, bioabsorbable mesh, at least one bioabsorbable alginate sheet, or a combination thereof. According to one embodiment, the support layer is suturable. According to one embodiment, the support layer is absorbed by surrounding tissue after the top and basement layer are at least partially absorbed. According to one embodiment, the support layer is porous. According to one embodiment, each layer is secured to a neighboring layer via a tissue glue or tissue adhesive. According to one embodiment, the alcohol composition includes from about 90% to about 100% ethanol. According to one embodiment, the cross-linking solution includes from about 0.01% to about 3% glutaraldehyde.

According to another aspect, a multilayer bioabsorbable construct is provided that includes:
  (a) at least one top layer including at least one amnion membrane layer;
  (b) at least one chorion membrane layer;
  (c) at least one basement layer including at least one amnion membrane layer; and
  (d) at least one support layer between the chorion membrane layer and basement layer. According to one embodiment, the support layer is porous. According to one embodiment, the support layer comprises bioabsorbable gauze, bioabsorbable mesh, at least one bioabsorbable alginate sheet, or a combination thereof. According to one embodiment, the support layer is suturable. According to one embodiment, the support layer is absorbed by surrounding tissue after the top and basement layer are at least partially absorbed. According to one embodiment, each layer is secured to a neighboring layer via a tissue glue or tissue adhesive. According to one embodiment, at least one or both the amnion membrane layer and chorion membrane layer is/are crosslinked.

According to one aspect, a method of treating pelvic organ prolapse in a subject is provided. The method includes the steps of providing a multilayer bioabsorbable construct as provided herein and implanting the construct in or around a subject's uterus, vaginal wall, or a combination thereof, to reinforce a weakened vaginal wall. According to one embodiment, the multilayer bioabsorbable construct is sutured in or around the uterus, vaginal wall, or a combination thereof.

According to one aspect, a method of treating stress urinary incontinence in a subject is provided. The method includes the steps of providing a multilayer bioabsorbable construct as provided herein and implanting the construct in or around a subject's urethra, bladder neck, or a combination thereof, to support the urethra and keep the urethra closed. According to one embodiment, the multilayer bioabsorbable construct is sutured in or around the urethra, bladder neck, or a combination thereof.

According to one aspect, a method of repairing or replacing a damaged tissue is provided. The method includes the steps of providing a multilayer bioabsorbable construct as provided herein and contacting the damaged tissue with the multilayer bioabsorbable construct. According to one embodiment, the damaged tissue is a wound. According to one embodiment, the wound is a burn, diabetic ulcer, decubitus ulcer, venous leg ulcer, arterial leg ulcer, or cutaneous ulcer. According to one embodiment, the step of contacting the damaged tissue includes implanting the construct into a cavity created as a result of a surgical procedure.

According to one aspect, a kit is provided. The kit includes at least one multilayer bioabsorbable construct as provided herein and at least one set of instructions for use thereof.

According to one aspect, a method of repairing or treating a defect in dura mater is provided. The method includes the steps providing a multilayer bioabsorbable construct as provided herein and implanting the multilayer bioabsorbable construct proximate to the defect in the dura mater. According to one embodiment, the dura mater surrounds the brain. According to one embodiment, the dura mater surrounds the spinal cord. According to one embodiment, the dura mater defect arises as a result of surgical intervention. According to one embodiment, the surgical intervention is a posterior fossa decompression procedure to repair Chiari malformation.

BRIEF DESCRIPTION OF THE DRAWINGS

FIG. 1 is a schematic illustration of a bioabsorbable multilayer construction according to one embodiment.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used in the specification, and in the appended claims, the words "optional" or "optionally" mean that the subsequently described event or circumstance can or cannot occur.

As used herein, the terms "bioabsorbable", "bioresorbable" and "biodegradable" may be used interchangeably and each refer to a material that dissolves in the body without causing a substantial immunological rejection or response.

As used herein, the term "human birth tissue" includes, but is not limited to, elements of the placental organ such as, for example, the placental globe, the umbilical cord, the umbilical cord blood, the chorion membrane layer, the amnion membrane layer, the amniotic fluid, and other placental gelatins, fluids, cells and extracellular material obtained from a seronegative, healthy human.

As used herein, the term "placental tissue components" include amnion membrane layer, chorion membrane layer, Wharton's jelly, umbilical cord tissue, placental globe, other gelatins, other cells and extracellular matrix from human birth tissue.

As used herein, the term "membrane" refers to an amnion membrane layer, a chorion membrane layer, or both a chorionic and an amnion membrane layer.

The present disclosure generally relates to a multilayer bioabsorbable construct and the use of such a construct in various therapeutic applications. The multilayer bioabsorbable construct demonstrates superior structural integrity, which allows the construct to be suturable while remaining bioabsorbable. Thus, the risk of rejection and subsequent complications (infections, inflammation, pain, shrinkage, etc.) are substantially reduced or eliminated. The present disclosure further relates to methods for aseptically processing human birth tissue to produce such multilayer bioabsorbable constructs.

According to one embodiment, the multilayer bioabsorbable construct includes multiple layers of human birth tissue. Each human birth tissue layer is processed in a manner provided herein and then assembled to form a single construct. According to such an embodiment, the resulting multilayer construct may be cut or otherwise sized to substantially cover, fill, or wrap a treatment area (e.g., damaged tissue, surgical site, organ).

According to one embodiment, the multilayer bioabsorbable construct includes at least one bottom or basement layer that includes: (i) at least one amnion membrane layer, at least one chorion membrane layer, or at least one of both an amnion and chorion membrane layer that is/are processed in a manner that includes treatment with at least one alcohol composition such as, for example, 90% to about 100% ethanol; or (ii) at least one cross-linked amnion membrane layer, at least one cross-linked chorion membrane layer, or at least one of both a cross-linked amnion and cross-linked chorion membrane layer that is/are processed in a manner that includes treatment with a cross-linking solution such as, for example, glutaraldehyde; or (iii) at least one amnion membrane layer that is processed in a manner that includes treatment with at least one alcohol composition such as, for example, 90% to about 100% ethanol coupled with a fresh chorion membrane layer; or (iv) at least one cross-linked amnion membrane layer coupled with a fresh chorion membrane layer. According to one embodiment, the multilayer bioabsorbable construct includes more than one bottom layer as provided herein.

According to one embodiment, the multilayer bioabsorbable construct includes at least one final or top layer that includes: (i) at least one amnion membrane layer, at least one chorion membrane layer, or at least one of both an amnion and chorion membrane layer that is/are processed in a manner that includes treatment with at least one alcohol composition such as, for example, 90% to about 100% ethanol; or (ii) at least one cross-linked amnion membrane layer, at least one cross-linked chorion membrane layer, or at least one of both a cross-linked amnion and cross-linked chorion membrane layer that is/are processed in a manner that includes treatment with a cross-linking solution such as, for example, glutaraldehyde; or (iii) at least one amnion membrane layer that is processed in a manner that includes treatment with at least one alcohol composition such as, for example, 90% to about 100% ethanol coupled with a fresh chorion membrane layer; or (iv) at least one cross-linked amnion membrane layer coupled with a fresh chorion membrane layer. According to one embodiment, the multilayer bioabsorbable construct includes more than one top layer as provided herein.

According to one embodiment, the multilayer bioabsorbable construct as provided herein includes at least one support layer below the top layer and above the bottom layer (i.e., in a middle portion of the construct). The support layer provides structural integrity to the construct. The support layer includes non-human birth tissue material that is bioabsorbable and suturable. According to one embodiment, the support layer is porous such that the surrounding layers may imbed or otherwise migrate or push through the support layer to an opposite side of the support layer. According to one embodiment, the support layer aids the construct in conforming to an area of treatment. According to one embodiment, the support layer is cuttable. According to one embodiment, the support layer is flexible. According to one embodiment, the support layer is hemostatic. According to one embodiment, the support layer is moldable.

According to one embodiment, the support layer is located within the multilayer bioabsorbable construct such that the support layer may not be exposed to the surrounding tissue at the treatment location until a certain timeframe after the basement layer and/or top layer(s) of the construct is absorbed by the surrounding tissue. According to one embodiment, the layers surrounding the support layer completely surround or form an envelope around the support layer. A delay in direct exposure of the support layer to the surrounding tissue allows the treatment location to benefit from the healing cascade aided initially by the surrounding construct layers. By placing the support layer within the construct, the incidence of immunological response and rejection associated with typical non-autologous or synthetic materials is reduced.

According to a particular embodiment, the support layer is formed from a bioabsorbable gauze. According to a particular embodiment, the support layer is formed from a bioabsorbable mesh. According to a particular embodiment, the support layer is formed from a bioabsorbable gel foam. According to a particular embodiment, the support layer is formed from a bioabsorbable alginate sheet. According to such an embodiment, the alginate sheet may transform to a moist gel after the construct is applied to a treatment area. The alginate sheet further provides a physiologically moist microenvironment that promotes healing and the formation of granulation tissue.

The multilayer bioabsorbable construct as provided herein may include multiple variations in the types of layers and number of layers. According to a particular embodiment, the multilayer bioabsorbable construct as provided herein includes at least one basement layer, at least one top layer, and at least one support layer with each of the aforementioned three layers repeated at least two or more times to form a multilayer bioabsorbable construct of at least six or more layers.

According to the embodiment of FIG. 1, the multilayer bioabsorbable construct 100 includes, from top to bottom the following layers: (a) at least one top layer 110 that includes at least one amnion membrane layer; (b) at least one chorion membrane layer 120; (c) at least one support layer 130; (d) and at least one basement layer 140 that includes at least one amnion membrane layer. The order of the aforementioned four-layer embodiment may be varied or may be repeated multiple times. Any of the layers that include human birth tissue may be fresh, frozen, crosslinked, treated with alcohol, or all prior to or after assembly.

Each layer of the multilayer bioabsorbable construct as provided herein may be assembled by any variety of methods such that the layers are stacked and stabilized to form a construct physically capable of performing the therapeutic uses provided herein. According to one embodiment, each layer (top membrane, support layer, basement membrane) is flattened out and cut to a target size and shape. The basement membrane is then placed on a flat surface. The next membrane or support layer is then placed on a top surface of the basement membrane. The placement of layers on top of one another (i.e., the stacking of layers) continues until the desired number of layers and thickness is achieved. According to one embodiment, each layer is optionally secured to a neighboring layer via a tissue glue, tissue adhesive or suture. Such a tissue glue, tissue adhesive or suture may be used alone or in combination with at least one support layer. The membranes included in the construct may be chemically bonded or crosslinked to one another to provide stability.

The multilayer bioabsorbable construct as described herein may be of various sizes, thickness, and shapes. The multilayer bioabsorbable construct as described herein can be produced at a desired size or produced in large sheets and cut to sizes deemed appropriate for the type of treatment. The multilayer bioabsorbable construct is preferably of sufficient size and shape to be applied onto or around a treatment area that is on or in a patient's body. The multilayer bioabsorbable construct thickness may vary depending on application, the type of membranes utilized, and the number of membrane and support layers. Typically, the wound covering is from about 0.05 mm to about 1.5 mm thick. The multilayer bioabsorbable construct as described herein may be stable at ambient temperature.

The multilayer bioabsorbable construct as provided herein includes human birth tissue material. To obtain such material, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorion membrane layer and amnion membrane layer), other gelatins, fluids, cells and extracellular matrix can be recovered from a seronegative, healthy human after the newborn is removed. The placental globe, umbilical cord, other gelatins, fluids, cells and extracellular matrix can be removed and discarded.

The membranes included in the multilayer bioabsorbable construct as described herein may be produced by processing human birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of the particular membrane is identified to ensure that in use the correct side of the membrane is placed on the wound. Either the fetal side or the maternal side of the membrane may be used depending upon the specific use or procedure that is being performed. The recovered amnion membrane layer, chorion membrane layer, or both amnion and chorion membrane layer may be initially stored in a sterile saline solution at a temperature between about 1° C. to about 10° C. for a period of up to about 120 hours prior to further processing. According to one embodiment, the sterile saline solution comprises from about 0.09% to about 20% NaCl.

According to one embodiment, the multilayer bioabsorbable construct includes at least one top or basement layer that is prepared by the following steps:
agitating the basin to liberate excess blood and fluids from the membrane;
rinsing the membrane with a sterile saline solution;
covering the membrane with a substrate on both the fetal membrane side and the maternal membrane side;
optionally, rinsing the membrane with a sterile saline solution;
optionally, soaking the membrane in a sterile saline solution;
immersing the membrane in an alcohol composition for a period of from about 1 second to about 384 hours;
removing the substrate from both the fetal membrane side and the maternal membrane side;
spreading the membrane on a flat, dry and sterile surface;
allowing the membrane to air dry completely at ambient temperature for a period of up to three hours;
cutting the membrane to a predetermined size to form at least one top or basement layer of the multilayer construct.

According to one embodiment, the multilayer bioabsorbable construct includes at least one top or basement layer that is prepared by the following steps:
agitating the basin to liberate excess blood and fluids from the membrane;
rinsing the membrane with a sterile saline solution;
covering the membrane with a substrate on both the fetal membrane side and the maternal membrane side;
immersing the membrane in a preservative solution for a period of up to about 20 minutes, wherein the preservative solution comprises from about 0.01% to about 3% of a cross-linking solution such as, for example, glutaraldehyde;
optionally, rinsing the membrane with a sterile saline solution;
optionally, soaking the membrane in a sterile saline solution;
immersing the membrane in an alcohol composition for a period of from about 1 second to about 384 hours;
removing the substrate from both the fetal membrane side and the maternal membrane side;
spreading the membrane on a flat, dry and sterile surface;
allowing the membrane to air dry completely at ambient temperature for a period of up to three hours;
cutting the membrane to a predetermined size to form at least one top or basement layer of the multilayer construct.

According to one embodiment, the multilayer bioabsorbable construct may then be optionally sealed in a vacuum chamber for up to about three hours. According to one embodiment, the multilayer bioabsorbable construct may then be placed in a desiccant cabinet. According to one embodiment, the multilayer bioabsorbable construct may remain the desiccant cabinet for at least one hour. According to a particular embodiment, the multilayer bioabsorbable construct may remain in the desiccant cabinet for up to about two hours. According to one embodiment, the relative humidity of the desiccant cabinet may be maintained at about 10% to about 30%. According to one embodiment, the relative humidity of the desiccant cabinet may be maintained at about 20%. The multilayer bioabsorbable construct may then be removed from the desiccant cabinet and cut to various sizes. According to a particular embodiment, the shape may be an oval ring having dimension of about 2 cm by about 3 cm. According to one embodiment, a crease down the centerline may be introduced for increased handling performance. The construct may then be packaged, sealed, and sterilized as provided herein.

The multilayer bioabsorbable construct as provided herein can be terminally sterilized using irradiation. In one embodiment, an electron beam irradiation is applied in an amount up to about 45 kGy. The sterilized construct may be stored for up to typically about two years from the date of processing. In one embodiment, the construct may be stored under proper conditions for as much as about five years following processing. According to a preferred embodiment, the construct may be stored under proper conditions for two years following processing. The sterilized construct may be stored in any container suitable for long-term storage. Preferably, the construct is stored in a sterile double peel-pouch package.

According to one embodiment, the multilayer bioabsorbable construct as provided herein can be used in various therapeutic capacities. According to one embodiment, the multilayer bioabsorbable construct can be secured into position to serve a therapeutic purpose via a variety of techniques well-known to those skilled in the art depending on the area of use. Suitable techniques, include, but are not limited to, tissue glue/adhesives (e.g., fibrin glue), sutures or staples. According to a particular embodiment, the support layer provides the requisite support and rigidity for the construct to be secured at the area of treatment with bioabsorbable sutures.

According to one embodiment, the multilayer bioabsorbable construct as provided herein can be used to repair or replace various types of tissue throughout the human body. The multilayer bioabsorbable construct can be contacted with the skin (e.g., epidermal applications) in any medically-acceptable manner that tends to facilitate healing of a defect in or on the skin. The multilayer bioabsorbable construct as provided herein can be placed on or in a persistent wound. The wound may arise in a variety of forms including, but not limited to, a burn, diabetic ulcer, decubitus ulcer, venous leg ulcer, arterial leg ulcer, or cutaneous ulcer.

According to one embodiment, the multilayer bioabsorbable construct as provided herein can be used to repair wounds arising on or around a soft tissue, nerve, organ, vascular tissue, muscle, spinal cord, bone, oral cavity, ocular surface, or a combination thereof. According to one embodiment, the multilayer bioabsorbable construct as provided herein may be used as a wound covering or an anti-adhesion barrier, for example, in surgical procedures including, but not limited to, spine surgeries, knee surgeries, shoulder surgeries, OB/GYN procedures, urological procedures, plastic surgeries, trauma-related cases, cardiovascular procedures, brain/neurological procedures, sport injury surgeries, soft tissue repair, burn and wound care.

According to a particular embodiment, the multilayer bioabsorbable construct as provided herein can be used as a substitute for urogynecologic surgical mesh to provide additional support when repairing weakened or damaged gynecological tissue or urological tissue. The multilayer bioabsorbable construct as provided herein reduces or prevents the complications that have arisen previously with vaginal mesh such as, for example, mesh erosion through the vagina (also called exposure, extrusion or protrusion), pain, infection, bleeding, pain during sexual intercourse (dyspareunia), organ perforation, urinary problems, recurrent prolapse, neuro-muscular problems, vaginal scarring/shrinkage, and emotional problems. Many of these complications have required additional intervention, including medical or surgical treatment and hospitalization.

According to one embodiment, the multilayer bioabsorbable construct as provided herein is particularly useful in treatment of urological and gynecologic disorders. According to one embodiment, a method of treating pelvic organ prolapse is provided. Pelvic organ prolapse occurs when the tissues that hold the pelvic organs in place become weak or stretched. The method includes the steps of providing the multilayer bioabsorbable construct as provided herein and permanently implanting the construct in or around the uterus, vaginal wall, or a combination thereof, to reinforce the weakened vaginal wall. According to one embodiment, the multilayer bioabsorbable construct is sutured in or around the uterus, vaginal wall, or a combination thereof.

According to one embodiment, a method of treating stress urinary incontinence is provided. Stress urinary incontinence is a leakage of urine during moments of physical activity, such as coughing, sneezing, laughing, or exercise. The method includes the steps of providing the multilayer bioabsorbable construct as provided herein and permanently implanting the construct in or around the urethra, bladder neck, or a combination thereof. According to one embodiment, the multilayer bioabsorbable construct is sutured in or around the urethra or bladder neck (sling procedure).

According to one embodiment, the multilayer bioabsorbable construct as provided herein is particularly useful as a dural implant or dural substitute. According to a particular embodiment, the multilayer bioabsorbable construct aids in the treatment and prevention of complications arising from surgical interventions for chiari malformation. In a typical Chiari malformation surgery, a surgeon removes a small section of bone at the back of the skull to make room for part of the brain (cerebellum) and relieves pressure on the brainstem, cerebellum and spinal cord to create more room for the cerebellar tonsils (e.g., posterior fossa decompression). A reconstructive operation of the open dura mater is often required and requires a dural substitute or graft (e.g., duraplasty). Many dural substitutes have been previously used with mixed results, including bovine grafts, human cadaveric pericardium, synthetic dura, and autologous pericranium. The multilayer bioabsorbable construct as provided herein is flexible, yet functional enough to create room for the cerebellar tonsils by expanding the potential space posterior to the hindbrain at the foramen magnum yet structurally potent enough to provide a tight closure to substantially reduce, eliminate or prevent post-operative spinal fluid leakage and ingress of blood and contaminants. The physical attributes of the multilayer bioabsorbable construct further reduce, eliminate or prevent meningitis, wound breakdown, adhesion formation, arachnoid scarring or inflammatory response.

A method of repairing or treating a defect in the dura mater of a patient is also provided. The method includes the step of providing the multilayer bioabsorbable construct as provided herein. The method further includes the step of implanting the multilayer bioabsorbable construct proximate to the defect in the dura mater. According to one embodiment, the dura mater surrounds the brain. According to one embodiment, the dura mater surrounds the spinal cord. According to one embodiment, the dura mater defect arises as a result of surgical intervention. According to a particular embodiment, the surgical intervention is a posterior fossa decompression procedure as a result of Chiari malformation.

A kit for use by a medical professional is also provided. According to one embodiment, the kit includes one or more packaged multilayer bioabsorbable constructs as provided herein. The kit may further include at least one set of instructions. The kit may further include a container adapted to accommodate and preserve the aforementioned components per applicable Food and Drug Administration guidelines. According to a particular embodiment, the kit includes individual construct layer materials that may be packaged individually and shipped together for assembly at the time of use. According to a particular embodiment, the kit includes in a single construct ready for implantation upon opening the package. According to one embodiment, the kit may include one or more components to aid the surgical professional in assembly and/or implantation including sutures or tissue glue/adhesive.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

I claim:

1. A method of repairing or replacing damaged tissue in a subject, comprising the steps of:
   providing a multilayer bioabsorbable construct comprising
      at least one top layer including at least one amnion membrane layer;
      at least one chorion membrane layer;
      at least one bottom layer including at least one amnion membrane layer; and
      at least one support layer completely enveloped between the chorion membrane layer and the bottom layer; and
   contacting the damaged tissue with the multilayer bioabsorbable construct,
   wherein the support layer comprises a moldable, porous bioabsorbable alginate sheet.

2. The method of claim 1, wherein the step of contacting the damaged tissue includes implanting the construct into a cavity created as a result of a surgical procedure.

3. A method of treating pelvic organ prolapse in a subject, comprising the steps of:
   providing a multilayer bioabsorbable construct comprising at least one top layer including at least one amnion membrane layer;

at least one chorion membrane layer;

at least one bottom layer including at least one amnion membrane layer; and at least one support layer completely enveloped between the chorion membrane layer and the bottom layer; and implanting the construct in or around a subject's uterus, vaginal wall, or a combination thereof, to reinforce a weakened vaginal wall, wherein the support layer comprises a moldable, porous bioabsorbable alginate sheet.

4. The method of claim 3, wherein the multilayer bioabsorbable construct is sutured in or around the uterus, vaginal wall, or a combination thereof.

\* \* \* \* \*